United States Patent
Chadeayne

(10) Patent No.: US 11,332,441 B2
(45) Date of Patent: May 17, 2022

(54) CRYSTALLINE N-METHYL TRYPTAMINE DERIVATIVES

(71) Applicant: CAAMTECH LLC, Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 16/827,072

(22) Filed: Mar. 23, 2020

(65) Prior Publication Data

US 2021/0300870 A1 Sep. 30, 2021

(51) Int. Cl.
*C07D 209/16* (2006.01)

(52) U.S. Cl.
CPC ........ *C07D 209/16* (2013.01); *C07B 2200/13* (2013.01)

(58) Field of Classification Search
CPC .......................... C07D 209/16; C07B 2200/13
USPC ......................................................... 514/415
See application file for complete search history.

(56) References Cited

U.S. PATENT DOCUMENTS

| | | | |
|---|---|---|---|
| 10,933,073 B2 * | 3/2021 | Chadeayne | A61K 31/352 |
| 2018/0221396 A1 * | 8/2018 | Chadeayne | A61P 25/24 |
| 2019/0142851 A1 * | 5/2019 | Chadeayne | A61K 31/675 514/80 |
| 2021/0292278 A1 * | 9/2021 | Chadeayne | A61K 31/4045 |

FOREIGN PATENT DOCUMENTS

| | | | | |
|---|---|---|---|---|
| WO | WO-2019073379 A1 * | 4/2019 | | A61K 47/38 |
| WO | WO-2021089873 A1 * | 5/2021 | | A61P 25/00 |

OTHER PUBLICATIONS

Andrew Chadeayne et al the fumarate salts of N-isopropyl-N-methyl derivatives of DMT and psilocin (Year: 2019).*
Simon Brandt et al Analytic chemistry of synthetic routes topsychoactive tryptamines. (Year: 2005).*
Lindsay Cameron et al Dark Classics in Chemical Neuroscience:N,N-Dimethyltryptamine (DMT) (Year: 2018).*
Chadeayne et al N-Methyl-N-propyltryptoamine (Year: 2019).*
David Nichols et al . Improvements to the synthesis of Psilocybin and a facile method for preparing the 0-acetyl prodrug of Psilocin. (Year: 1999).*
Repke; J. Med. Chem. 1985, 28, 7, 892-896. (Year: 1985).*
Repke; J. Het. Chem. 1981, 18, 175-179. (Year: 1981).*
Aixala, M., Dos Santos, R. G., Hallak, J. E. C. & Bouso, J. C. (2018). ACS Chem. Neurosci. 9, 2304-2306.
Bradley, R. J. & Johnston, V. S. (1970). Origin and Mechanism of Hallucinations, edited byW. Keup, pp. 333-344. New York: Plenum Press.
Dameron, L. P., Benson, C. J., DeFelice, B. C., Fiehn, O. & Olson, D. E. (2019). ACS Chem. Neurosci. In the press. http://doi.org/10.1021/acschemneuro.8b00692.
Carhart-Harris, R. L., Bolstridge, M., Rucker, J., Day, C. M., Erritzoe, D., Kaelen, M., Bloomfield, M., Rickard, J. A., Forbes, B., Feilding, A., Taylor, D., Pilling, S., Curran, V. H. & Nutt, D. J. (2016) Lancet Psychiatr. 3, 619-627.
Carhart-Harris, R. L. & Goodwin, G. M. (2017). Neuropsychopharmacology, 42, 2105-2113.
Dinis-Oliveira, R. J. (2017). Drug Metab. Rev. 49, 84-91.
Falkenberg, G. (1972). Acta Cryst. B28, 3075-3083.
Fontanilla, D., Johannessen, M., Hajipour, A. R., Cozzi, N. V., Jackson, M. B. & Ruoho, A. E. (2009). Science, 323, 934-937.
Gilman, A.; Hardman, J.; Limbird, L. eds., Goodman and Gilman's "The Pharmacological Basis of Therapeutics," Tenth Edition, McGraw-Hill Press, 155-173 (2001).
Johnson, M. W. & Griffiths, R. R. (2017). Neurotherapeutics, 14, 734-740.
Manske, R. H. F. (1931). Can. J. Res. 5, 592-600.
Mckenna, D. J., Repke, D. B., Lo, L. & Peroutka, S. J. (1990). Neuropharmacology, 29,193-198.
Nichols, D. E. (2012). WIREs Membr. Transp. Signal. 1, 559-579.
Nichols, D. E. (2016). Pharmacol. Rev. 68, 264-355.
Passie, T., Seifert, J., Schneider, U. & Emrich, H. M. (2002). Addict. Biol. 7, 357-364.
Petcher, T. J. & Weber, H. P. (1974). J. Chem. Soc. Perkin Trans. II, pp. 946-948.
Neber, H. P. & Petcher, T. J. (1974). J. Chem. Soc. Perkin Trans. II, pp. 942-946.

* cited by examiner

*Primary Examiner* — Daniel R Carcanague
(74) *Attorney, Agent, or Firm* — J.A. Lindeman & Co., PLLC

(57) ABSTRACT

Crystalline N-methyl tryptamine derivatives, compositions containing those crystalline forms and their methods of use are disclosed. The crystalline N-methyl tryptamine derivatives according to the invention include crystalline N-methyl-N-propyltryptamine (MPT), crystalline N-methyl-N-isopropyltryptammonium fumarate (MiPT fumarate) and crystalline 4-hydroxy-N-methyl-N-isopropyltryptammonium fumarate monohydrate (HO-MiPT fumarate monohydrate).

18 Claims, 11 Drawing Sheets

CRYSTALLINE N-METHYL TRYPTAMINE DERIVATIVES

FIELD OF THE INVENTION

This invention relates to crystalline N-methyl tryptamine derivatives, compositions containing those crystalline forms and their methods of using the same. The crystalline N-methyl tryptamine derivatives according to the disclosure include crystalline N-methyl-N-propyltryptamine (MPT), crystalline N-methyl-N-isopropyltryptammonium fumarate (MiPT fumarate), and/or crystalline 4-hydroxy-N-methyl-N-isopropyltryptammonium fumarate monohydrate (HO-MiPT fumarate monohydrate).

BACKGROUND OF THE INVENTION

N-methyl-N-propyltryptamine (MPT) is a structural analog of N,N-dimethyltryptamine (DMT), which is a well-known 'psychedelic' molecule found in a variety of naturally occurring organisms, including plants, animals, and fungi, including mushrooms. In humans, DMT is the only known endogenous mammalian N,N-dimethylated trace amine (Fontanilla et al., 2009). Naturally occurring tryptamines (e.g. DMT, psilocybin, 5-methoxy-N,N-dimethyltryptamine) and their synthetic derivatives (e.g. psilacetin, MPT) have garnered considerable attention of late due to new evidence demonstrating their efficacy in treating mood (e.g. anxiety and depression) and post-traumatic stress disorders (PTSDs) (Aixala` et al., 2018; Cameron et al., 2019).

Psilocybin, isolated from the so-called "magic" mushrooms, is perhaps the best-known prodrug of the serotonin 2a agonist psilocin (Nichols, 2016). Recent studies indicate that psilocin (and its prodrugs like psilocybin and psilacetin) could provide effective treatment for mood disorders, end-of-life anxiety, addiction, and PTSD (Carhart-Harris et al., 2016; Johnson & Griffiths, 2017). However, the long duration of action of psilocin and its prodrugs can result in practical challenges for both patients and clinicians (Passie et al., 2002). Accordingly, the mental health industry would benefit from exploring alternative tryptamine treatment options that provide similar therapeutic benefits while having a shorter duration of action.

While the synthesis of DMT was first reported in 1931 (Manske, 1931), the first literature report of MPT appeared in 2005 (Brandt et al., 2005) and it has not undergone significant study. Prior to this work, however, no crystalline form of MPT has been reported. There is a need therefore to develop a form of MPT that allows for development as an active pharmaceutical ingredient (an API) and for pharmaceutical compositions containing that form of MPT. This disclosure answers such needs.

Although therapeutic efficacy is the primary concern for an active pharmaceutical ingredient (API), the salt and solid state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY OF THE DISCLOSURE

This disclosure relates to new crystalline forms of N-methyl tryptamine derivatives, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate).

In one embodiment, crystalline N-methyl-N-propyltryptamine (MPT) according to the disclosure is characterized by an orthorhombic, Pbca crystal system space group at a temperature of about 200 K; unit cell dimensions a=13.5715 (11) Å, b=12.4352(10) Å, c=15.1627(12) Å, at a temperature of about 200 K; an x-ray powder diffraction (XRPD) pattern substantially similar to FIG. 3; or an x-ray powder diffraction (XRPD) pattern having peaks at 11.7, 13.4 and 19.4°2θ±0.2° 2θ.

In one embodiment, crystalline N-methyl-N-isopropyltryptammonium fumarate (MiPT fumarate) according to the disclosure is characterized by a monoclinic, P2$_1$/c crystal system space group at a temperature of about 200 K; unit cell dimensions a=9.852 (2) Å, b=12.789(2) Å, c=14.875 (3) Å, and β=106.932 (7°) at a temperature of about 200 K; an x-ray powder diffraction pattern substantially similar to FIG. 7; or an x-ray powder diffraction (XRPD) pattern having peaks at 11.9, 14.9 and 16.9°2θ±0.2° 2θ.

In one embodiment, crystalline 4-hydroxy-N-methyl-N-isopropyltryptammonium fumarate monohydrate (HO-MiPT fumarate monohydrate) according to the disclosure is characterized by a monoclinic, C2/c crystal system space group at a temperature of about 200 K; unit cell dimensions a=29.507 (3) Å, b=8.7445(8) Å, c=17.3659 (18) Å, and β=123.389 (18°) at a temperature of about 200 K; an x-ray powder diffraction pattern substantially similar to FIG. 11; or an x-ray powder diffraction (XRPD) pattern having peaks at 7.2, 13.4 and 18.0°2θ±0.2° 2θ.

The disclosure also relates to compositions comprising a crystalline N-methyl tryptamine derivative according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), and an excipient.

The disclosure also relates to compositions comprising a combination of, as a first component, a crystalline N-methyl tryptamine derivative according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), and a second component selected from (a) a purified psilocybin derivative, (b) one or two purified cannabinoids, and (c) a purified terpene.

The disclosure further relates to methods of treatment preventing or treating a physical and/or psychological disorder comprising the step of administering to a subject in need thereof an effective amount of a crystalline N-methyl tryptamine derivative according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), or a composition according to the disclosure.

The disclosure also relates to methods of preventing or treating inflammation and/or pain comprising the step of administering to a subject in need thereof an effective amount of a crystalline N-methyl tryptamine derivative according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), or a composition according to the disclosure.

DETAILED DESCRIPTION

Figure 1:
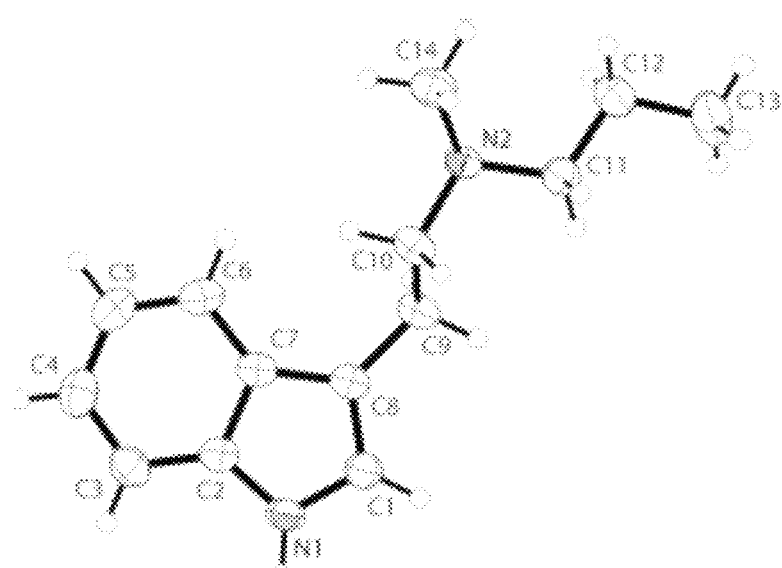
FIG. 1 depicts the molecular structure of crystalline MPT according to the disclosure with atomic labelling.

This disclosure relates to crystalline N-methyl tryptamine derivatives, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), and to pharmaceutical compositions containing a crystalline N-methyl tryptamine derivative according to the disclosure. The therapeutic uses of the crystalline N-methyl tryptamine derivatives according to the disclosure, are described below as well as compositions containing them. The crystalline N-methyl tryptamine derivatives according to the disclosure, and the methods used to characterize it are described in the examples below.

Methods of Treatment and Therapeutic Uses

In one embodiment, the crystalline N-methyl tryptamine derivatives according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), the methods and the pharmaceutical compositions of the disclosure are used to regulate the activity of a neurotransmitter receptor by administering a therapeutically effective dose of a crystalline N-methyl tryptamine derivative of the disclosure. In another embodiment, the crystalline N-methyl tryptamine derivatives according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), the methods and the pharmaceutical compositions of the disclosure are used to treat inflammation and/or pain by administering a therapeutically effective dose of a crystalline form of N-methyl tryptamine derivatives of the disclosure. Methods of the disclosure administer a therapeutically effective amount of a crystalline N-methyl tryptamine derivative of the disclosure to prevent or treat a disease or condition such as those discussed below for a subject in need of treatment. A crystalline N-methyl tryptamine derivative of the disclosure may be administered neat or as a composition comprising a crystalline N-methyl tryptamine derivative of the disclosure as discussed below.

A crystalline N-methyl tryptamine derivative of the disclosure may be used to prevent and/or treat a psychological disorder. The disclosure provides a method for preventing and/or treating a psychological disorder by administering to a subject in need thereof a therapeutically effective amount of a crystalline N-methyl tryptamine derivative of the disclosure, including the preferred embodiments discussed above. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

A crystalline N-methyl tryptamine derivative of the disclosure may be used to prevent and/or treat of a brain disorder. The disclosure provides a method for preventing and/or treating a brain disorder by administering to a subject in need thereof a therapeutically effective amount of a crystalline N-methyl tryptamine derivative of the disclosure, including the preferred embodiments discussed above. The brain disorder is chosen from Huntington's disease, Alzheimer's disease, dementia, and Parkinson's disease.

A crystalline N-methyl tryptamine derivative of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a crystalline N-methyl tryptamine derivative of the disclosure, including the preferred embodiments discussed above.

A crystalline form of N-methyl tryptamine derivatives of the disclosure may be used to prevent and/or treat inflammation and/or pain, such as for example inflammation and/or pain associated with inflammatory skeletal or muscular diseases or conditions. The disclosure provides a method for preventing and/or treating a inflammation and/or pain by administering to a subject in need thereof a therapeutically effective amount of a crystalline form of N-methyl tryptamine derivatives of the disclosure, including the preferred embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendonopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compositions

The disclosure also relates to compositions comprising an effective amount of a crystalline N-methyl tryptamine derivative of the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), especially pharmaceutical compositions comprising a therapeutically effective amount of a crystalline N-methyl tryptamine derivative of the disclosure and a pharmaceutically acceptable carrier (also known as a pharmaceutically acceptable excipient). As discussed above, a crystalline N-methyl tryptamine derivative of the disclosure may be, for example, therapeutically useful to prevent and/or treat the psychological and other disorders discussed above.

A composition or a pharmaceutical composition of the disclosure may be in any form which contains a crystalline N-methyl tryptamine derivative of the disclosure. The composition may be, for example, a tablet, capsule, liquid suspension, injectable, topical, or transdermal. The compositions or pharmaceutical compositions generally contain, for example, about 1% to about 99% by weight of a crystalline N-methyl tryptamine derivative of the disclosure and, for example, 99% to 1% by weight of at least one suitable pharmaceutical excipient. In one embodiment, the composition may be between about 5% and about 75% by weight of a crystalline N-methyl tryptamine derivative of the disclosure with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, crystalline N-methyl tryptamine derivatives according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate), may be used as the "first purified psilocybin derivative" in the compositions described in US 2018/0221396 A1 and US 2019/0142851 A1. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments. Accordingly, the disclosure provides a composition comprising as a first component: a crystalline N-methyl tryptamine derivative according to the disclosure, specifically crystalline N-methyl-N-propyltryptamine (MPT), crystalline N-methyl-N-isopropyltryptammonium fumarate (MiPT fumarate) or crystalline 4-hydroxy-N-methyl-N-isopropyltryptammonium fumarate monohydrate (HO-MiPT fumarate monohydrate); and as a second component selected from (a) a purified psilocybin derivative, (b) one or two purified cannabinoids and (c) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder or condition as described herein.

An "effective amount" or a "therapeutically effective amount" of a crystalline N-methyl tryptamine derivative according to the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. A crystalline N-methyl tryptamine derivative according to the disclosure, compositions and pharmaceutical compositions containing it may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the crystalline N-methyl tryptamine derivative or produce undesirable biological effects or otherwise interact in a deleterious manner with any other component(s) of the pharmaceutical composition.

The compositions or pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, the crystalline N-methyl tryptamine derivative may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of a crystalline N-methyl tryptamine derivative of the disclosure in pure form, with a permeation enhancer, with stabilizers (e.g. antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

Single Crystal X-Ray Diffraction (SCXRD) Characterization: Data were collected on a Bruker D8 Venture CMOS Diffractometer equipped with an Oxford Cryosystems Cryostream cooling device and using Mo Kα radiation. Structures were solved using the Bruker SHELXTL program and refined with the SHELXTL program as part of the Bruker SHELXTL suite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Example 1: Preparation and Characterization of Crystalline N-methyl-N-propyltryptamine (MPT)

Crystal Preparation

Single crystals suitable for X-ray analysis were obtained from the slow evaporation of a methylene chloride solution of a commercial sample of N-methyl-N-propyltryptamine (MPT) (The Indole Shop, Canada).

Single Crystal X-Ray Diffraction (SCXRD) Characterization

The single crystal data and structure refinement parameters for the crystalline structure measured at 200 K are reported in Table 1, below.

TABLE 1

Experimental Details

| Crystal Data | |
| --- | --- |
| Chemical formula | $C_{14}H_{20}N_2$ |
| $M_r$ | 216.32 |
| Crystal system, space group | Orthorhombic, Pbca |
| Temperature (K) | 200 |
| a, b, c (Å) | 13.5715 (11), 12.4352 (10), 15.1627 (12) |
| V (Å$^3$) | 2558.9 (4) |
| Z | 8 |
| Radiation Type | Mo Kα |
| μ (mm$^{-1}$) | 0.07 |
| Crystal size (mm) | 0.28 × 0.20 × 0.13 |
| Data collection | |
| Diffractometer | Bruker D8 Venture CMOS |
| Absorption correction | Multi-scan (SADABS; Bruker, 2016) |
| $T_{min}$, $T_{max}$ | 0.713, 0.745 |
| No. of measured, independent and observed [I > 2σ(I)] reflections | 47431, 2350, 1942 |
| $R_{int}$ | 0.048 |
| (sin θ/λ)$_{max}$(Å$^{-1}$) | 0.604 |
| Refinement | |
| R[F$^2$ > 2σ(F$^2$)], wR(F$^2$), S | 0.036, 0.095, 1.05 |
| No. of reflections | 2350 |
| No. of parameters | 152 |
| H-atom treatment | H atoms treated by a mixture of independent and constrained refinement |
| Δρ$_{max}$, Δρ$_{min}$ (eÅ$^{-3}$) | 0.17, −0.16 |

Computer programs: APEX3 and SAINT (Bruker, 2016), SHELXT2014 (Sheldrick, 2015a), SHELXL2014 (Sheldrick, 2015b), publCIF (Westrip, 2010) and OLEX2 (Dolamanov et al, 2009).

Figure 2:
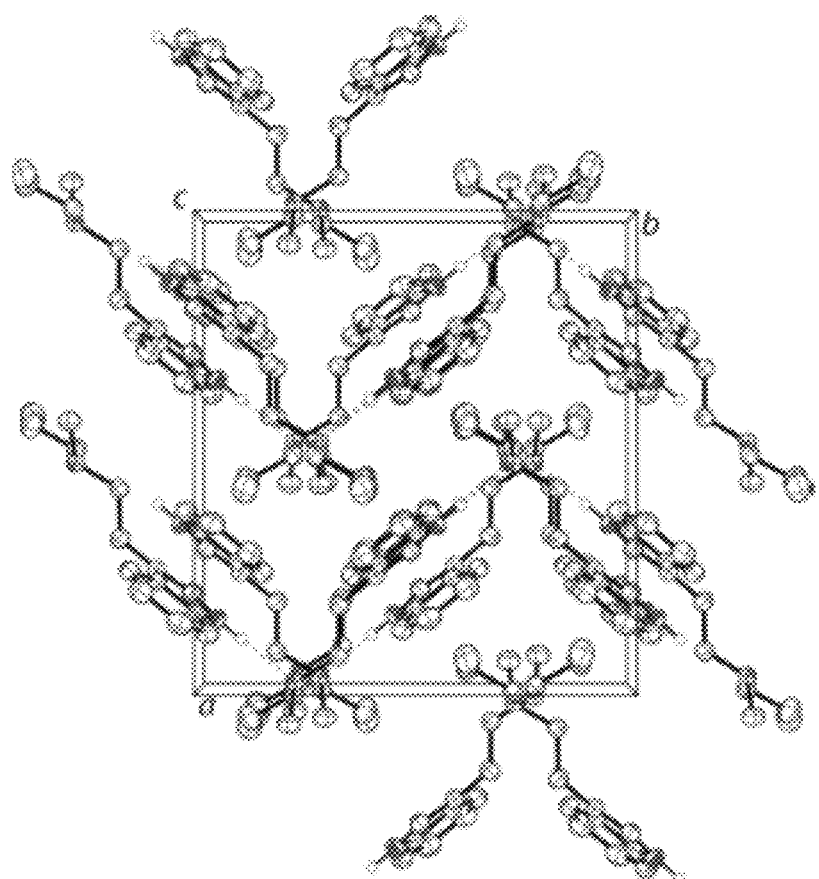
FIG. 2 shows the crystal packing of crystalline MPT, viewed along the c axis.

The molecular structure of crystalline MPT according to the disclosure is shown in FIG. 1 with atomic labelling. Displacement ellipsoids are drawn at the 50% probability level. FIG. 2 shows the crystal packing of crystalline MPT, viewed along the c axis. The N—H—N hydrogen bonds are shown as dashed lines. Displacement ellipsoids are drawn at the 50% probability level. H atoms not involved in hydrogen bonding have been omitted for clarity.

In the solid-state structure of MPT, there is a single molecule in thesymmetric unit, with an indole group that demonstrates a mean deviation from planarity of 0.015 Å (FIG. 1). The metrical parameters are consistent with the previously reported structure of DMT (Falkenberg, 1972) and other dialkyltryptamines (Chadeayne et al., 2019a,b; Petcher & Weber, 1974; Weber & Petcher, 1974). The tryptamine molecules are held together in an infinite one-dimensional chain along [010] through N—HN hydrogen bonds connecting the indole N atom to themine N atom (Table 1, FIG. 2). In the structure of N,N-dimethyltryptamine (DMT), there are similar hydrogen bonds, but they hold molecules together as dimers rather than in a chain. There are no π-π interactions observed in the crystalline DMT structure.

Figure 3:
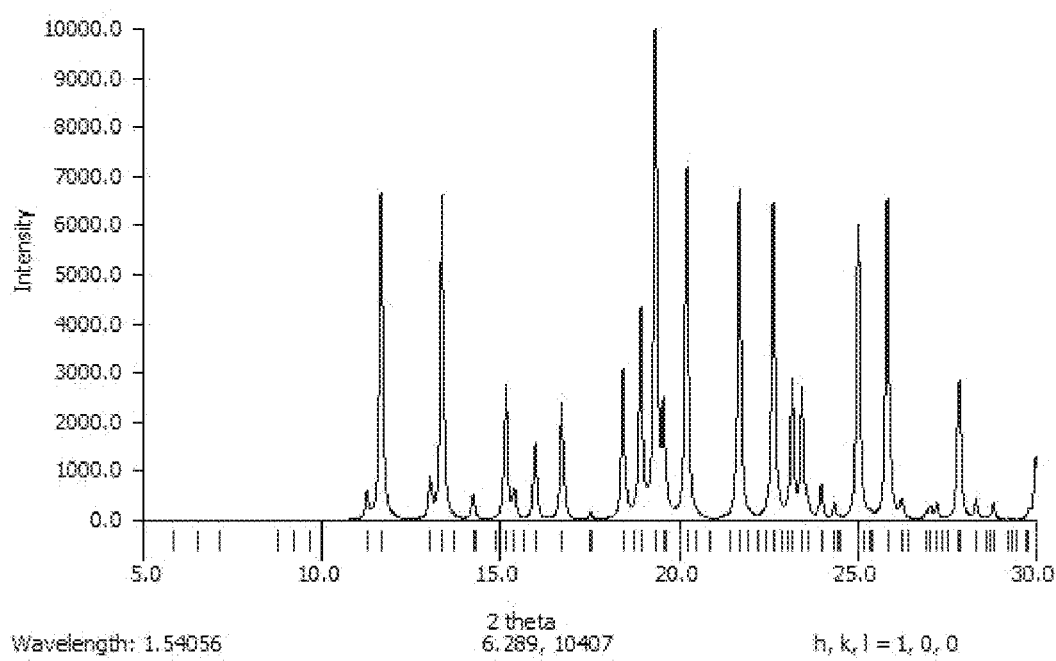
FIG. 3 is a simulated X-ray powder diffraction pattern (XRPD) for crystalline MPT generated from its single crystal data.

FIG. 3 is a simulated X-ray powder diffraction pattern (XRPD) for crystalline MPT generated from its single crystal data. Characteristic peaks identifying crystalline MPT include peaks at 11.7, 13.4 and 19.4°2θ±0.2° 2θ.

Example 2: Preparation and Characterization of Crystalline N-methyl-N-isopropyltryptammonium fumarate (MiPT fumarate) and 4-hydroxy-N-methyl-N-isopropyltryptammonium fumarate monohydrate (HO-MiPT fumarate monohydrate)

Crystal Preparation

Single crystals suitable for X-ray analysis were obtained from the slow evaporation of aqueous solutions of commercial samples of N-methyl-N-isopropyltryptammonium fumarate and 4-hydroxy-N-methyl-N-isopropyltryptammonium fumarate monohydrate (The Indole Shop, Canada).

Single Crystal X-Ray Diffraction (SCXRD) Characterization

The single crystal data and structure refinement parameters for the crystalline structure measured at 200 K are reported in Table 2, below.

TABLE 2

Experimental Details

| | MiPT | 4-HO-MiPT |
| --- | --- | --- |
| Crystal Data | | |
| Chemical formula | $C_4H_3O_4 \cdot C_{14}H_{21}N_2$ | $C_{14}H_{21}N_2O \cdot H_2O \cdot C_4H_3O_4$ |
| $M_r$ | 332.39 | 366.41 |
| Crystal system, space group | Monoclinic, P2$_1$/c | Monoclinic, C2/c |
| Temperature (K) | 200 | 200 |
| a, b, c (Å) | 9.852 (2), 12.789 (2), 14.875 (3) | 29.507 (3), 8.7445 (8), 17.3659 (18) |
| β (°) | 106.932 (7) | 123.389 (3) |
| V(Å$^3$) | 1793.0 (6) | 3741.2 (7) |
| Z | 4 | 8 |
| Radiation Type | Mo Kα | Mo Kα |
| μ (mm$^{-1}$) | 0.09 | 0.10 |
| Crystal size (mm) | 0.20 × 0.18 × 0.05 | 0.30 × 0.25 × 0.20 |
| Data collection | | |
| Diffractometer | Bruker D8 Venture CMOS | Bruker D8 Venture CMOS |
| Absorption correction | Multi-scan (SADABS; Bruker, 2016) | Multi-scan (SADABS; Bruker, 2016) |
| $T_{min}$, $T_{max}$ | 0.687, 0.745 | 0.719, 0.745 |
| No. of measured, independent and observed [I > 2σ(I)] reflections | 36899, 3297, 2605 | 70395, 3458, 2978 |
| $R_{int}$ | 0.052 | 0.041 |
| (sinθ/λ)$_{max}$(Å$^{-1}$) | 0.604 | 0.604 |
| Refinement | | |
| R[F$^2$ > 2σ(F$^2$)], wR(F$^2$), S | 0.049, 0.127, 1.06 | 0.041, 0.096, 1.08 |
| No. of reflections | 3297 | 3458 |
| No. of parameters | 240 | 320 |
| No. of restraints | 8 | 12 |
| H-atom treatment | H atoms treated by a mixture of independent and constrained refinement | H atoms treated by a mixture of independent and constrained refinement |
| Δρ$_{max}$, Δρ$_{min}$ (eÅ$^{-3}$) | 0.26, −0.26 | 0.22, −0.20 |

Computer programs: Bruker APEX3, Bruker SAINT, SHELXS97 (Sheldrick 2008), XL (Sheldrick, 2008), Olex2 (Dolomanov et al., 2009).

Figure 4:
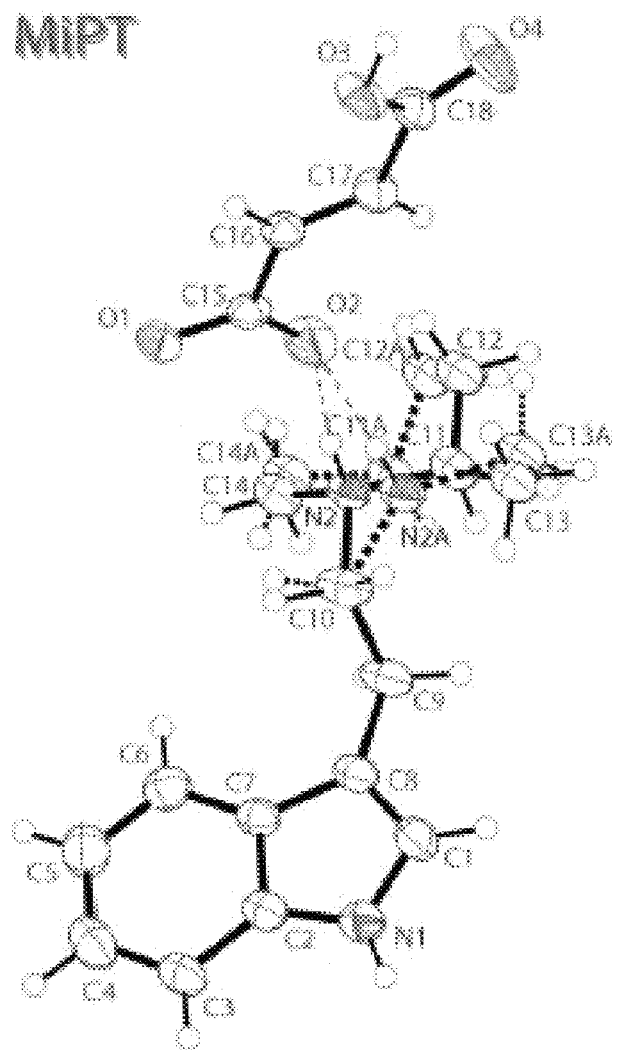
FIG. 4 shows the molecular structure of crystalline MiPT fumarate with atomic labelling.
Figure 5:
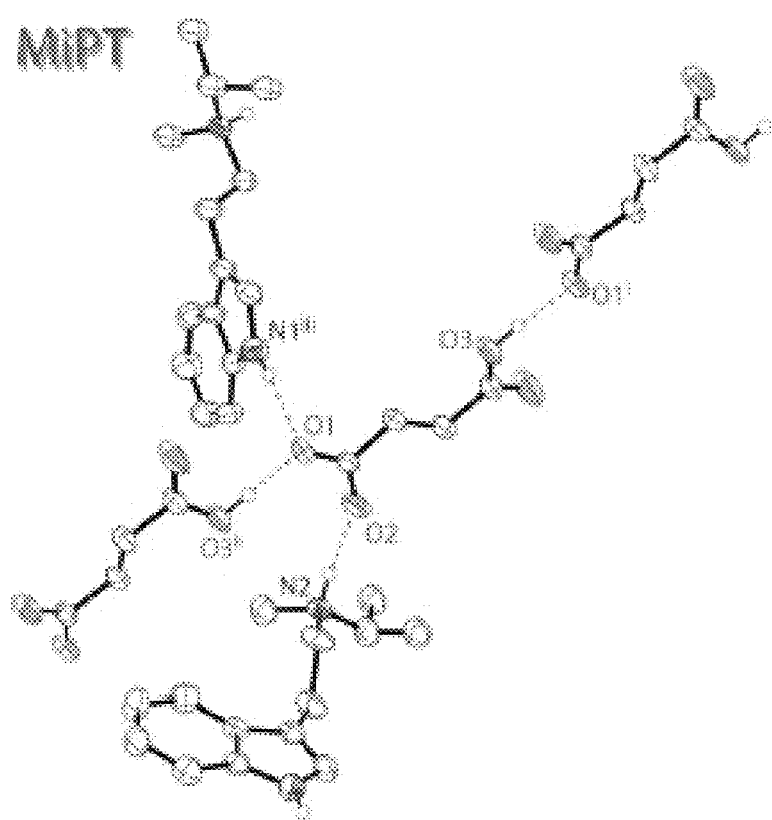
FIG. 5 shows the hydrogen bonding of the fumarate ion in the structure of crystalline MiPT fumarate.

The molecular structure of crystalline MiPT fumarate according to the disclosure is shown in FIG. 4 with atomic labelling, and the hydrogen bonding of the fumarate ion in the structure of crystalline MiPT fumarate is shown in FIG. 5. Displacement ellipsoids are drawn at the 50% probability level. The symmetric unit contains one N-methyl-N-isopropyltryptammonium ($C_{14}H_{21}N_2^+$) cation and one 3-carboxyacrylate ($C_4H_3O_4^-$) anion. The indole ring system of the cation is near planar with an r.m.s. deviation from planarity of 0.006 Å. The singly protonated fumarate anion is in the trans configuration and is slightly distorted from planarity with an r.m.s. deviation of 0.133 Å and a carboxylate twist angle of 18.370 (5). The N-methyl-N-isopropylammonium group is disordered over two orientations in a 0.630 (3): 0.370 (3) ratio.

In the extended crystal structure of MiPT fumarate, the N-methyl-N-isopropylamine and fumarate ions are linked into infinite two-dimensional networks lying parallel to the (010) plane through N—H—O and O—H—O hydrogen bonds. The proton of themmonium cation forms a hydrogen bond with one of the oxygen atoms of the deprotonated —$CO_2^-$ group of the 3-carboxyacrylate ion. The carboxylic acid proton forms a hydrogen bond with an oxygen atom of an adjacent 3-carboxyacrylate anion. The N—H grouping of the indole ring also hydrogen bonds to one of the oxygen atoms of the 3-carboxyacrylate anion.

Figure 6:
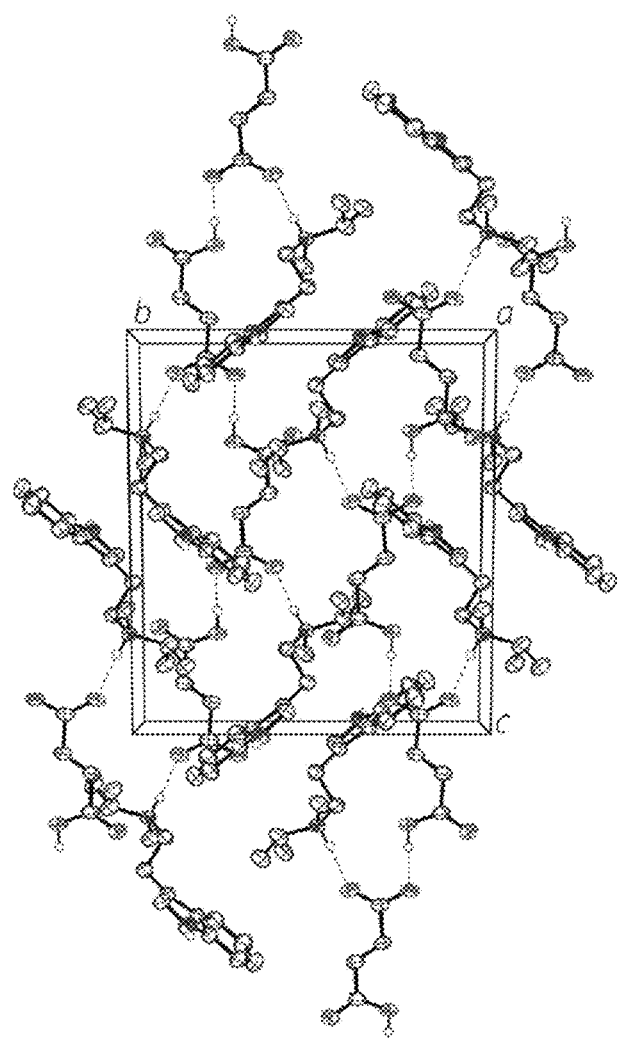
FIG. 6 shows the crystal packing of crystalline MiPT fumarate, viewed along the axis.

FIG. 6 shows the crystal packing of crystalline MiPT fumarate, viewed along the axis. The hydrogen bonds are shown as dashed lines. Displacement ellipsoids are drawn at the 50% probability level. H atoms not involved in hydrogen bonding have been omitted for clarity.

Figure 7:
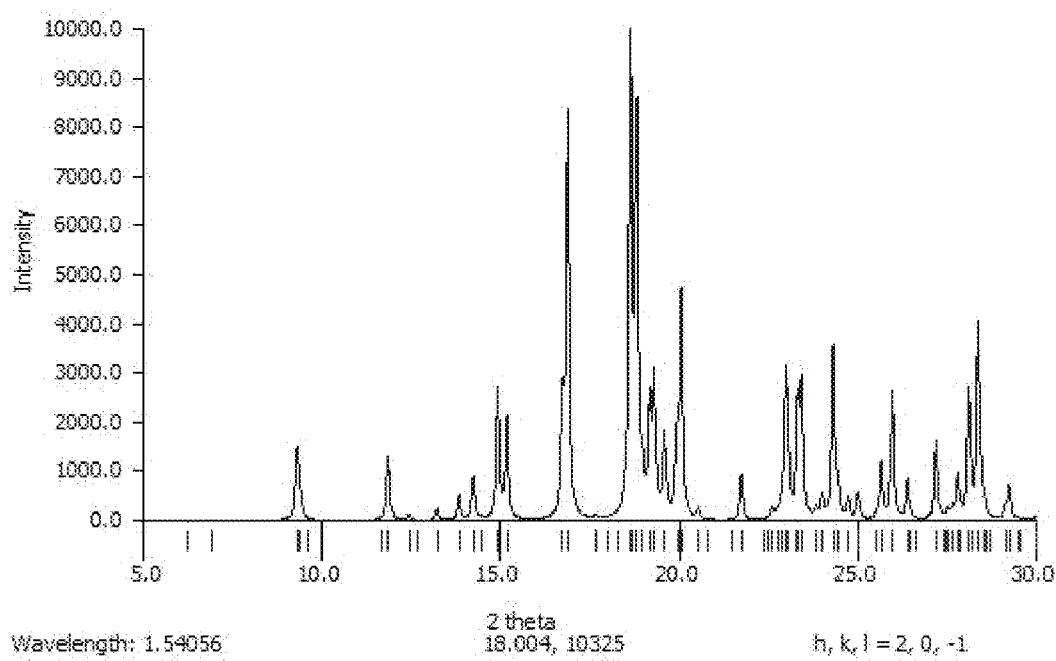
FIG. 7 is a simulated X-ray powder diffraction pattern (XRPD) for crystalline MiPT fumarate generated from its single crystal data.

FIG. 7 is a simulated X-ray powder diffraction pattern (XRPD) for crystalline MiPT fumarate generated from its single crystal data. Characteristic peaks identifying crystalline MiPT include peaks at 11.9, 14.9 and 16.9°2θ±0.2° 2θ.

Figure 8:
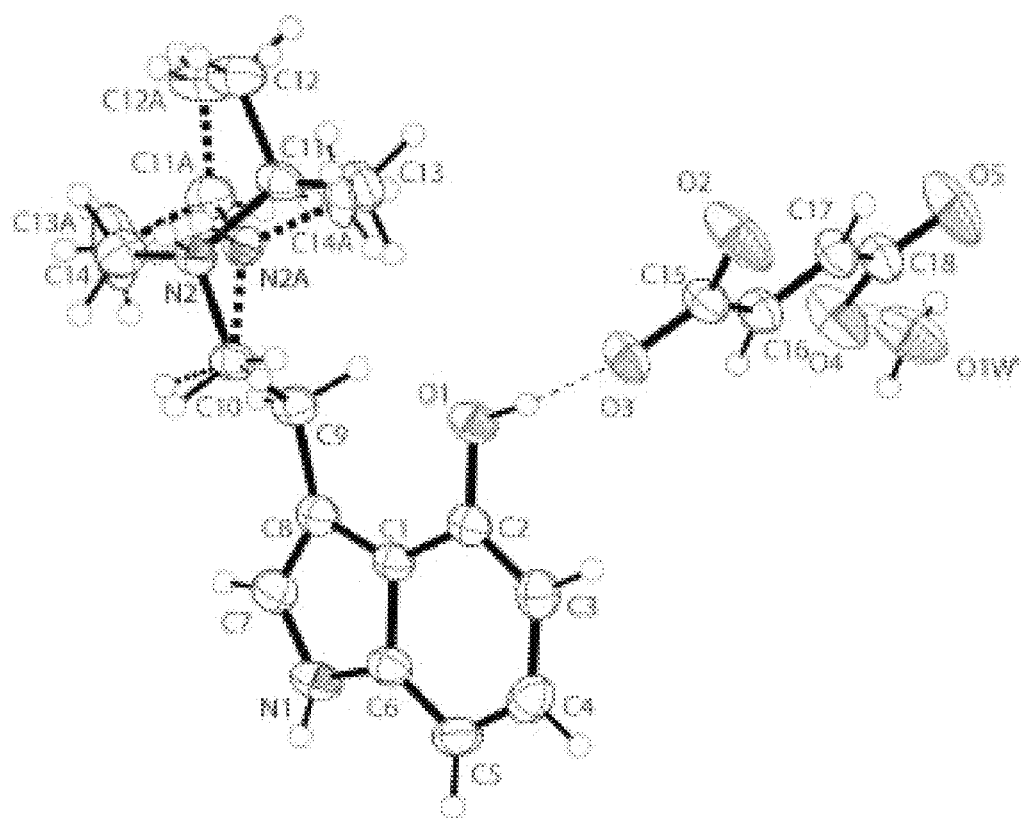
FIG. 8 shows the molecular structure of crystalline HO-MiPT fumarate monohydrate with atomic labelling.
Figure 9:
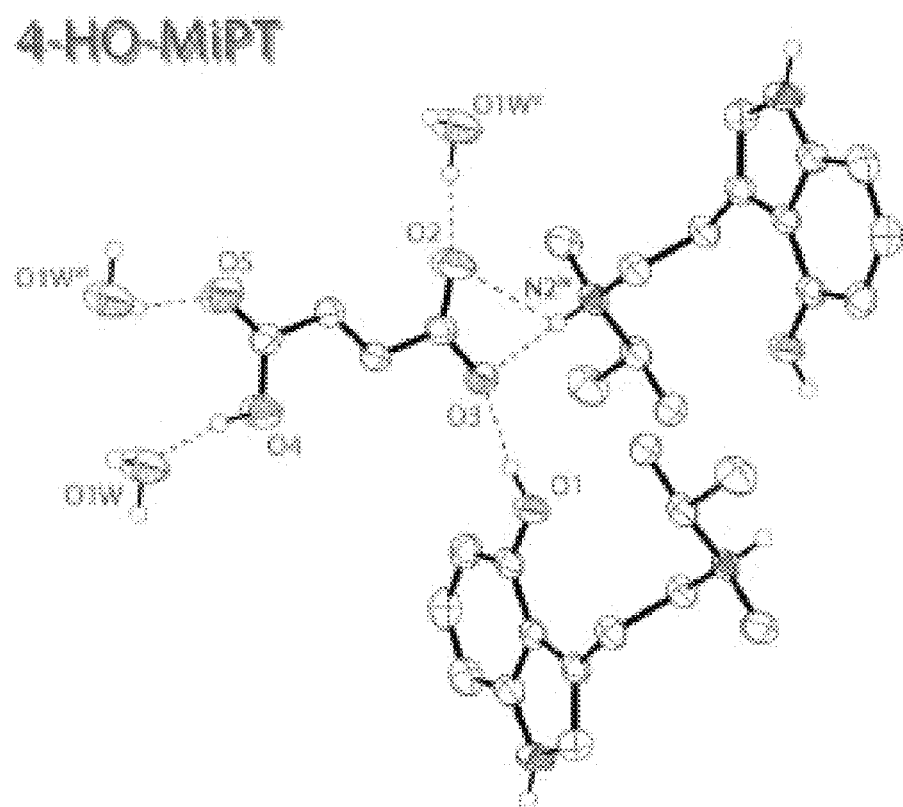
FIG. 9 shows the hydrogen bonding of the fumarate ion in the structure of crystalline MiPT fumarate.

The molecular structure of crystalline HO-MiPT fumarate monohydrate according to the disclosure is shown in FIG. 8 with atomic labelling, and the hydrogen bonding of the fumarate ion in the structure of crystalline MiPT fumarate is shown in FIG. 9.

Displacement ellipsoids are drawn at the 50% probability level. Thesymmetric unit contains one 4-hydroxy-N-methyl-N-isopropyltryptammonium ($C_{14}H_{21}N_2O^+$) cation, one 3-carboxyacrylate anion and one water molecule of crystallization. The indole ring system of the cation is close to planar with an r.m.s. deviation of 0.021 Å. The singly protonated fumarate anion is also near planar with an r.m.s. deviation of 0.049 Å. The N-methyl-Nisopropylammonium group shows a similar disorder to the MiPT structure over two orientations in a 0.775 (5):0.225 (5) ratio.

In the structure of 4-HO-MiPT fumarate monohydrate, there are N—H—O and O—H—O hydrogen bonds that link together the cations and anions as well as the water molecules of crystallization. The result is a two-dimensional network lying parallel to the (201) plane. The proton of themmonium cation forms a bifurcated N—H—(O,O) hydrogen bond with the deprotonated —$CO_2$ group of the 3-carboxyacrylate ion. The hydrogen of the hydroxy group also hydrogen bonds to the same oxygen atom of thenion. The carboxylic acid proton hydrogen bonds with a water molecule in the structure. Two other water molecules form hydrogen bonds with two different oxygen atoms of thenion.

Figure 10:
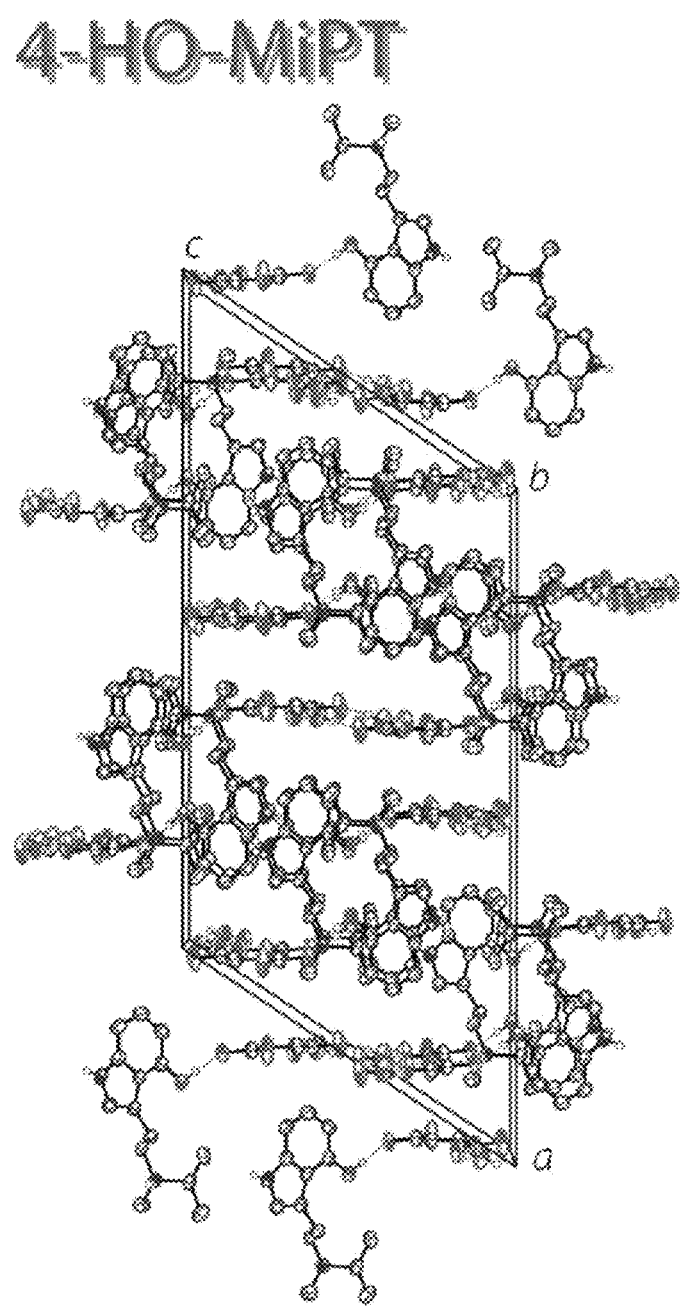
FIG. 10 shows the crystal packing of crystalline HO-MiPT fumarate monohydrate, viewed along the b axis.

FIG. 10 shows the crystal packing of crystalline HO-MiPT fumarate monohydrate, viewed along the b axis. The hydrogen bonds are shown as dashed lines. Displacement ellipsoids are drawn at the 50% probability level. H atoms not involved in hydrogen bonding have been omitted for clarity.

Figure 11:
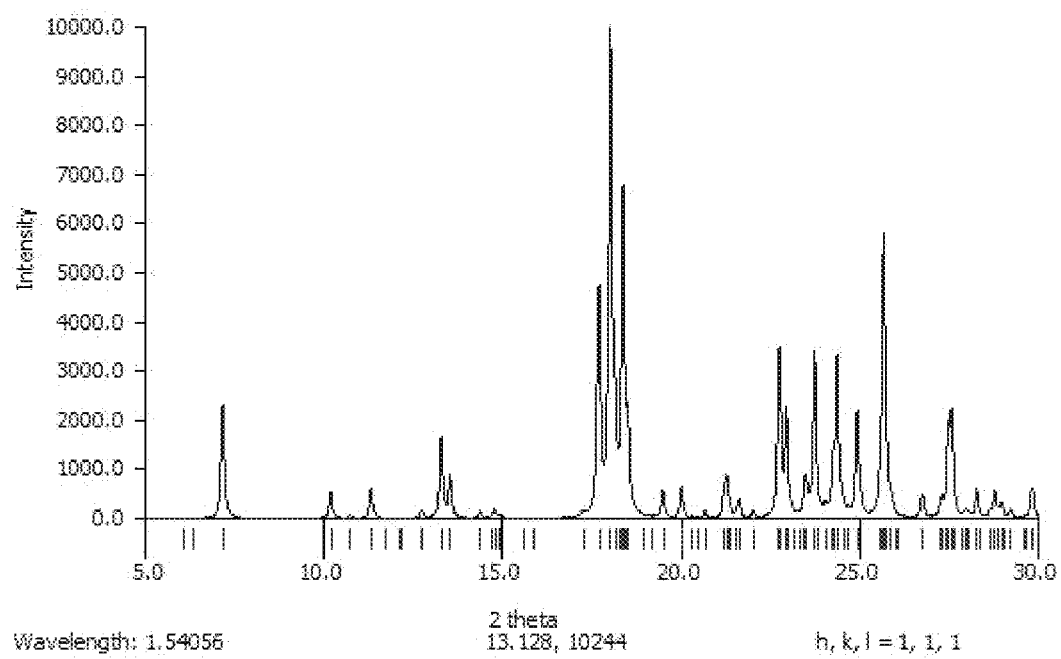
FIG. 11 is a simulated X-ray powder diffraction pattern (XRPD) for HO-MiPT fumarate monohydrate generated from its single crystal data.

FIG. 11 is a simulated X-ray powder diffraction pattern (XRPD) for HO-MiPT fumarate monohydrate generated from its single crystal data. Characteristic peaks identifying crystalline HO-MiPT include peaks at 7.2, 13.3 and 18.0°2θ±0.2° 2θ.

The MiPT structure described above is a derivative of DMT (N,N-dimethyltryptamine), which has been structurally characterized (Falkenberg, 1972), as well as its close derivative MPT, N-methyl-N-propyltryptamine (Chadeayne et al. 2019b). In both cases, these were crystallized as free bases, while MiPT is the fumarate salt. In the case of 4-HO-MiPT, the most closely related molecule is psilocin, which has been structurally characterized (Petcher & Weber, 1974), as well as psilocybin (Weber & Petcher, 1974). Psilocin was reported as the free base and psilocybin was reported as a zwitterionic molecule, while the structure of 4-HO-MiPT reported here is the hydrated fumarate salt. Two different ionic structures of the 4-acetoxy derivative of DMT have been reported as fumarate salts (Chadeayne et al. 2019a,c). The metrical parameters of the tryptammonium cations for MiPT and 4-HOMiPT are consistent with those of the other tryptammonium structures reported.

REFERENCES

1. Aixala`, M., Dos Santos, R. G., Hallak, J. E. C. & Bouso, J. C. (2018). ACS Chem. Neurosci. 9, 2304-2306.
2. Bradley, R. J. & Johnston, V. S. (1970). Origin and Mechanism of Hallucinations, edited by W. Keup, pp. 333-344. New York: Plenum Press.
3. Brandt, S. D., Freeman, S., Fleet, I. A., McGagh, P. & Alder, J. F. (2005). Analyst, 130, 330-344.
4. Bruker (2016). APEX3, SAINT, and SADABS. Bruker AXS Inc., Madison, Wis., USA.
5. Cameron, L. P. & Olson, D. E. (2018). ACS Chem. Neurosci. 9, 2344-2357.
6. Cameron, L. P., Benson, C. J., DeFelice, B. C., Fiehn, O. & Olson, D. E. (2019). ACS Chem. Neurosci. In the press. http://doi.org/10.1021/acschemneuro.8b00692.
7. Carhart-Harris, R. L., Bolstridge, M., Rucker, J., Day, C. M., Erritzoe, D., Kaelen, M., Bloomfield, M., Rickard, J. A., Forbes, B., Feilding, A., Taylor, D., Pilling, S., Curran, V. H. & Nutt, D. J. (2016). Lancet Psychiatr. 3, 619-627.
8. Carhart-Harris, R. L. & Goodwin, G. M. (2017). Neuropsychopharmacology, 42, 2105-2113.
9. Chadeayne, A. R., Golen, J. A. & Manke, D. R. (2019a). Acta Cryst. E75, 900-902.
10. Chadeayne, A. R., Golen, J. A. & Manke, D. R. (2019b). IUCrData, 4, x190962.
11. Chadeayne, A. R., Golen, J. A. & Manke, D. R. (2019c). Psychedelic Science Review, https://psychedelicreview.com/the-crystal-structure-of-4-aco-dmt-fumarate/12.
12. Dinis-Oliveira, R. J. (2017). Drug Metab. Rev. 49, 84-91.
13. Dolomanov, O. V., Bourhis, L. J., Gildea, R. J., Howard, J. A. K. & Puschmann, H. (2009). J. Appl. Cryst. 42, 339-341.
14. Falkenberg, G. (1972). Acta Cryst. B28, 3075-3083.
15. Fontanilla, D., Johannessen, M., Hajipour, A. R., Cozzi, N. V., Jackson, M. B. & Ruoho, A. E. (2009). Science, 323, 934-937.
16. Gilman, A.; Hardman, J.; Limbird, L. eds., Goodman and Gilman's "The Pharmacological Basis of Therapeutics," Tenth Edition, McGraw-Hill Press, 155-173 (2001).
17. Johnson, M. W. & Griffiths, R. R. (2017). Neurotherapeutics, 14, 734-740.
18. Manske, R. H. F. (1931). Can. J. Res. 5, 592-600.

19. McKenna, D. J., Repke, D. B., Lo, L. & Peroutka, S. J. (1990). Neuropharmacology, 29, 193-198.
20. Nichols, D. E. (2012). WIRES Membr. Transp. Signal. 1, 559-579.
21. Nichols, D. E. (2016). Pharmacol. Rev. 68, 264-355.
22. Passie, T., Seifert, J., Schneider, U. & Emrich, H. M. (2002). Addict. Biol. 7, 357-364.
23. Petcher, T. J. & Weber, H. P. (1974). J. Chem. Soc. Perkin Trans. II, pp. 946-948.
24. Repke, D. B., Ferguson, W. J. & Bates, D. K. (1981). J. Heterocycl. Chem. 18, 175-179.
25. Repke, D. B., Grotjahn, D. B. & Shulgin, A. T. (1985). J. Med. Chem. 28, 892-896.
26. Sheldrick, G. M. (2008). Acta Cryst. A64, 112-122.
27. Sheldrick, G. M. (2015a). Acta Cryst. A71, 3-8.
28. Sheldrick, G. M. (2015b). Acta Cryst. C71, 3-8.
29. Weber, H. P. & Petcher, T. J. (1974). J. Chem. Soc. Perkin Trans. II, pp. 942-946.
30. Westrip, S. P. (2010). J. Appl. Cryst. 43, 920-925.

The invention claimed is:

1. Crystalline N-methyl-N-propyltryptamine (MPT) characterized by one or more of:
    an orthorhombic, Pbca crystal system space group at a temperature of about 200 K;
    unit cell dimensions a=13.5715 (11) Å, b=12.4352(10) Å, c=15.1627(12) Å, at a temperature of about 200 K;
    or
    an x-ray powder diffraction (XRPD) pattern having peaks at 11.7, 13.4 and 19.4° 2θ±0.2° 2θ.

2. Crystalline N-methyl-N-propyltryptamine (MPT) according to claim 1, further characterized by an x-ray powder diffraction (XRPD) pattern substantially similar to FIG. 3.

3. A composition comprising crystalline N-methyl-N-propyltryptamine (MPT) according to claim 1 and an excipient.

4. A method of treating a psychological disorder comprising the step of:
    administering to a subject in need thereof a therapeutically effective amount of crystalline N-methyl-N-propyltryptamine (MPT) according to claim 1.

5. A method of treating a psychological disorder comprising the step of:
    administering to a subject in need thereof a therapeutically effective amount of crystalline N-methyl-N-propyltryptamine (MPT) according to claim 2.

6. A method of treating a psychological disorder comprising the step of:
    administering to a subject in need thereof a composition according to claim 3.

7. Crystalline N-methyl-N-isopropyltryptammonium fumarate (MiPT fumarate) characterized by one or more of:
    a monoclinic, P2$_1$/c crystal system space group at a temperature of about 200 K;
    unit cell dimensions a=9.852 (2) Å, b=12.789(2) Å, c=14.875 (3) Å, and β=106.932(7°) at a temperature of about 200 K;
    or
    an x-ray powder diffraction (XRPD) pattern having peaks at 11.9, 14.9 and 16.9° 2θ±0.2° 2θ.

8. Crystalline N-methyl-N-isopropyltryptammonium fumarate (MiPT fumarate) according to claim 7, further characterized by an x-ray powder diffraction (XRPD) pattern substantially similar to FIG. 2.

9. A composition comprising crystalline N-methyl-N-isopropyltryptammonium fumarate (MiPT fumarate) according to claim 7 and an excipient.

10. A method of treating a psychological disorder comprising the step of:
    administering to a subject in need thereof a therapeutically effective amount of crystalline N-methyl-N-isopropyltryptammonium fumarate (MiPT fumarate) according to claim 7.

11. A method of treating a psychological disorder comprising the step of:
    administering to a subject in need thereof a therapeutically effective amount of crystalline N-methyl-N-isopropyltryptammonium fumarate (MiPT fumarate) according to claim 8.

12. A method of treating a psychological disorder comprising the step of:
    administering to a subject in need thereof a composition according to claim 9.

13. Crystalline 4-hydroxy-N-methyl-N-isopropyltryptammonium fumarate monohydrate (HO-MiPT fumarate monohydrate) characterized by one or more of:
    a monoclinic, C2/c crystal system space group at a temperature of about 200 K;
    unit cell dimensions a=29.507 (3) Å, b=8.7445(8) Å, c=17.3659 (18) Å, and β=123.389(18°) at a temperature of about 200 K;
    or
    an x-ray powder diffraction (XRPD) pattern having peaks at 7.2, 13.4 and 18.0° 2θ±0.2° 2θ.

14. Crystalline 4-hydroxy-N-methyl-N-isopropyltryptammonium fumarate monohydrate (HO-MiPT fumarate monohydrate) according to claim 13, further characterized by an x-ray powder diffraction (XRPD) pattern substantially similar to FIG. 11.

15. A composition comprising crystalline 4-hydroxy-N-methyl-N-isopropyltryptammonium fumarate monohydrate (HO-MiPT fumarate monohydrate) according to claim 13 and an excipient.

16. A method of treating a psychological disorder comprising the step of:
    administering to a subject in need thereof a therapeutically effective amount of crystalline 4-hydroxy-N-methyl-N-isopropyltryptammonium fumarate monohydrate (HO-MiPT fumarate monohydrate) according to claim 13.

17. A method of treating a psychological disorder comprising the step of:
    administering to a subject in need thereof a therapeutically effective amount of crystalline 4-hydroxy-N-methyl-N-isopropyltryptammonium fumarate monohydrate (HO-MiPT fumarate monohydrate) according to claim 14.

18. A method of treating a psychological disorder comprising the step of:
    administering to a subject in need thereof a composition according to claim 15.

* * * * *